United States Patent [19]

Ehm et al.

[11] Patent Number: 4,569,225

[45] Date of Patent: Feb. 11, 1986

[54] TEST APPARATUS IN WHICH EXTREMELY HIGH TEST PRESSURES CAN BE GENERATED IN HOLLOW BODIES IN A FRACTION OF A SECOND

[75] Inventors: Karl Ehm, Neusaess; Wolfram Lausch, Augsburg, both of Fed. Rep. of Germany

[73] Assignee: M.A.N.-Roland Druckmaschinen Aktiengesellschaft, Offenbach am Main, Fed. Rep. of Germany

[21] Appl. No.: 661,655

[22] Filed: Oct. 17, 1984

[30] Foreign Application Priority Data

Oct. 20, 1983 [DE] Fed. Rep. of Germany ....... 3338128

[51] Int. Cl.[4] .............................................. G01M 3/02

[52] U.S. Cl. .......................................... 73/49.4; 74/55

[58] Field of Search ...................... 73/49.4, 168, 37 F; 74/55

[56] References Cited

U.S. PATENT DOCUMENTS

| | | | |
|---|---|---|---|
| 940,751 | 11/1909 | Thompson | 74/55 |
| 2,147,037 | 2/1939 | Hunefeld | 74/55 |
| 2,567,735 | 9/1951 | Scott | 74/55 |
| 2,725,742 | 12/1953 | Crooks | 73/49.4 |
| 4,318,446 | 3/1982 | Livesay | 74/55 |

*Primary Examiner*—Stewart J. Levy

*Assistant Examiner*—Hezron E. Williams

*Attorney, Agent, or Firm*—Frishauf, Holtz, Goodman & Woodward

[57] ABSTRACT

In the test apparatus for a hollow body having a volume of approximately 1 to 10 cubic decimeters (1 to 10 liters), pressures can be generated using a fluid medium which is compressible within the hollow body with a compressibility of down to 1% per 1000 bar pressure loading. This is attained by means of an apparatus for generating extreme pressure, which enables the buildup of pressures on the order of magnitude of 10,000 bar in the hollow body within a fraction of a second.

10 Claims, 5 Drawing Figures

7
64
5
8,9
65
12,13
10,11
16,17
59
60
56
1
19
18
58
57
15
61
6
14
2
4
3

CONTROL UNIT (CU)
COMMAND
h(5)
1
5
6
7
8
9
10
11
12
13
15
16
17
20
21
22
23
24
25
26
27
28
29
56
62
63

TEST APPARATUS IN WHICH EXTREMELY HIGH TEST PRESSURES CAN BE GENERATED IN HOLLOW BODIES IN A FRACTION OF A SECOND

The invention relates to a test apparatus in which test pressures can be generated in hollow bodies having a volume of between about 1 and 10 $dm^3$ (i.e., 1 to 10 liters), with the aid of a pressure medium. The pressure medium can be compressed within the hollow body with a compressibility of down to 1% per 1000 bar pressure loading. The apparatus includes a holder device for receiving a hollow body and retaining it in a fixed position during the application of pressure thereto.

BACKGROUND

Hollow bodies or units exposed during operation to extremely high working pressures, and in particular to pulsed pressures, must for safety reasons be monitored as to whether the wall of the hollow body or the unit is sufficiently strong. No apparatus has hitherto been known, however, which would have enabled the simulation of extremely high pressures which arise and disappear again within an extremely brief time.

THE INVENTION

It is accordingly an object of the invention to devise an apparatus with which pressures can be generated in hollow bodies, so that either the hollow bodies themselves or component units disposed in them can be monitored as to whether they meet the load requirements placed upon them or not.

Briefly, the apparatus comprises the combination of three basic assemblies or units, mainly (a) a drive unit having a fly wheel mounted on a main shaft, a motor driving the fly wheel, two control cams of mirror symmetrical shape secured to the main shaft, each control cam having a complete circular portion and a land portion axially adjacent the circular portion;

(b) a pressure generating unit having a pressure piston shaped to penetrate the hollow body and to be received therein with essentially no leakage of pressure fluid, the pressure piston being carried by a piston rod movably secured on the frame of the apparatus, the end remote from the pressure piston carrying a pair of cam follower rollers which are biased for engagement with respective ones of the control cams; and (c) an operating unit for selectively controlling, and effecting engagement of the respective cam follower roller, selectively, with the respective land portion of the control cams or with the circular portions of the control cams, in synchronism with rotation of the main shaft.

Upon control of the cam follower rollers to switch from the track or path of the cam which forms the circular portion to the path which includes the land portion, the pressure piston will be selectively operated to penetrate into the hollow body, and thus cause the compressive force to be exerted by the pressure fluid therein. This operation can then be carried out during a fraction of a second, the shift between the complete circular and the part circular and the land portion of the cam being controlled at respective positions of engagement of the cam follower rollers with the cams when the cam follower rollers are on entirely circular portions of the cam.

DRAWING

DETAILED DESCRIPTION

Figure 1:
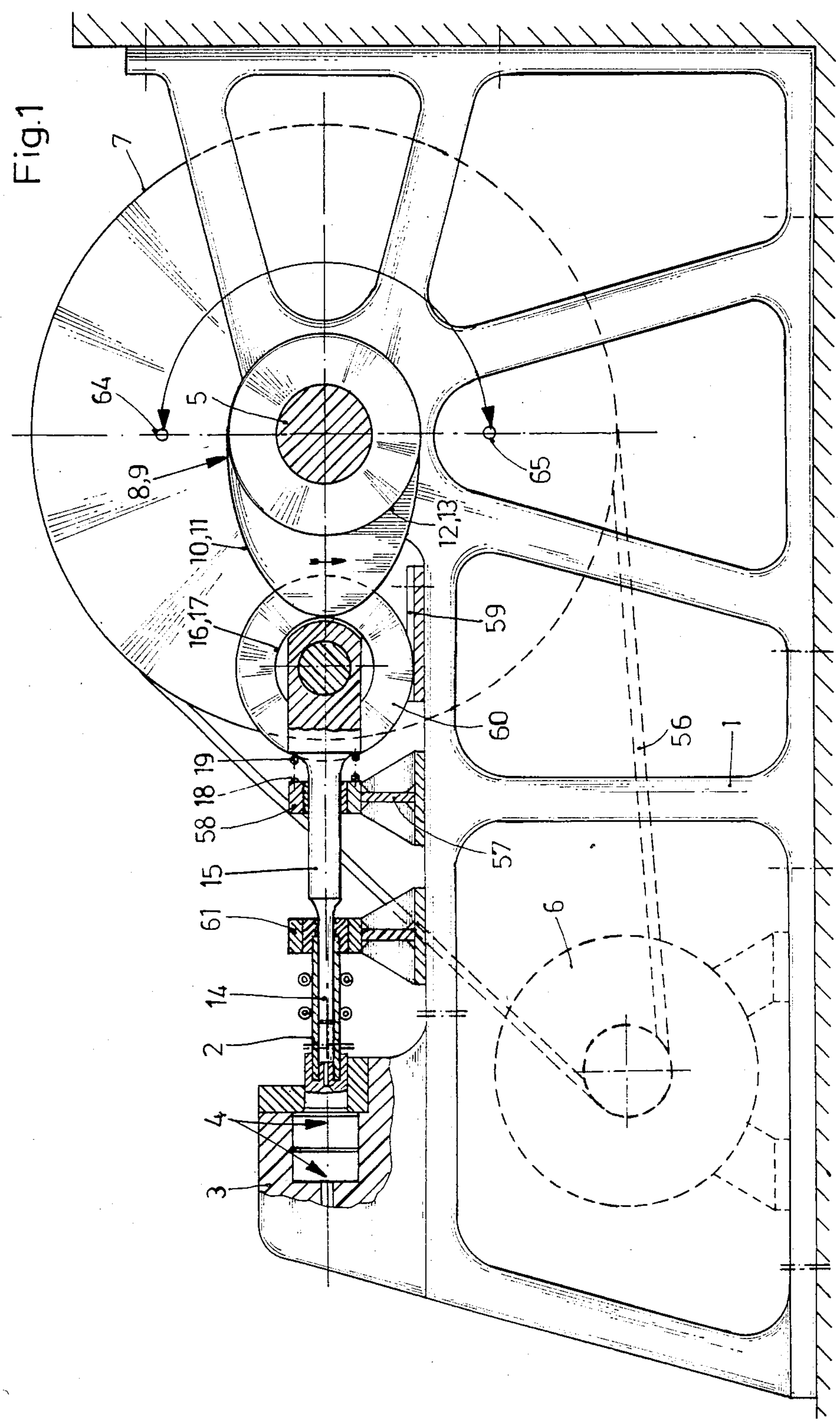
FIG. 1 is a side view of a test apparatus according to the invention, having a first exemplary embodiment of a device for generating extreme pressure.
Figure 2:
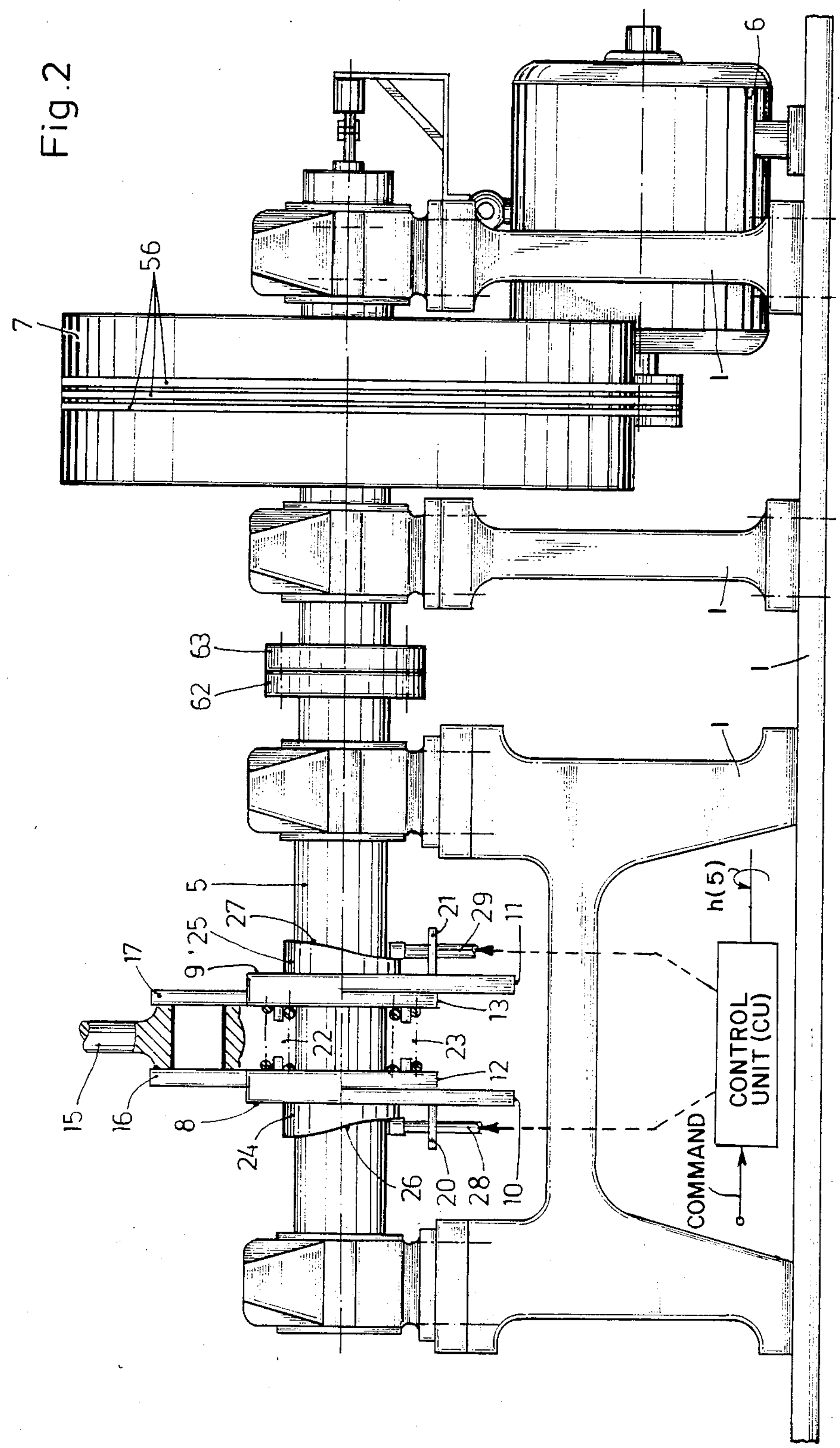
FIG. 2 is a side view of the test apparatus according to FIG. 1, in which, however, the elements executing the control of the pressure generation are shown not in their correct position but rather shifted by 90° into the plane of the drawing, in order to render details of the control area visible.

A test apparatus is shown in FIGS. 1 and 2 in which hollow bodies having a volume of approximately 1 to 10 $dm^3$, i.e., 1 to 10 liters, or component units disposed in such bodies, can be monitored, using a pressure fluid which can be compressed within the hollow body, with a compressibility of down to 1% per 1000 bar pressure loading. The test apparatus comprises a sturdy frame 1, which is installed in a stationary manner. Both the frame 1 and the hollow body 2 in which pressure is to be generated are shown in FIG. 1 with a shorter than actual proportionate length. A suitable test object holder 3 is provided on the frame 1, in which holder 3 a hollow body 2 is retained in a fixed position during the application of pressure thereto. The holder 3 contains not only clamping and position fixing means but also means 4 by which the fluid medium required for generating pressure can be introduced into the interior of the hollow body 2 and replenished in the event of any leakage losses. In accordance with the invention, a device for generating extreme pressure is now disposed on the test apparatus. This device enables the buildup, within a fraction of a second, for instance 50 msec, of pressures in a hollow body 2 that are on the order of magnitude of 10,000 bar and includes the following assemblies or units, to be described below, which are disposed on or in the frame 1:

(a) a drive unit having a fly wheel 7 mounted on the main shaft 5; a motor 6 driving the fly wheel 7; two control cams 8, 9 of mirror symmetrical shape secured to the main shaft 5, each control cam having a complete circular portion 12, 13 and a part circular, part land portion 10, 11 adjacent the complete circular portion;

(b) a pressure generating unit having means 4 for introducing a pressure fluid into the hollow body 2; a pressure piston 14 shaped to penetrate the hollow body and to be received therein with essentially no leakage of pressure fluid; a piston rod 15 movably secured on the frame 1 having one end thereof coupled to the pressure piston 14; a pair of cam follower rollers 16, 17 secured to the other end of the piston rod 15, a respective one of the cam follower rollers being biased for engagement with a respective one of the control cams 8, 9; and (c) an operating unit for selectively controlling and effecting engagement of the respective cam follower rollers 16, 17 with the respective land portions of the control cams 8, 9, or the entire circular portion of the control cams.

The apparatus according to characteristic (c) above, with which the part circular, part land portions 10, 11 and the cam follower rollers 16, 17 on the piston rod 15 can be brought into and out of control contact synchronously within a fraction of a second, may for instance be embodied as shown in detail in FIG. 2. The two control cams 8 and 9 are secured against twisting between two stops 20 and 21 firmly fixed on the frame 1 but are supported such that they are axially displaceable on the main shaft 5; they are spread apart by biased springs 22, 23. The main shaft 5 may have an axially parallel ribbing or splines in the area of displacement of the two control cams 8, 9; in that event, the through bores of the two control cams 8 and 9 must be ribbed or splined accordingly. On the outside of each control cam 8 or 9, there is a respective control disc 24 or 25, the end face of which includes a continuous control path 26 or 27 embodied such that the respective control cam 8 or 9 is displaceable with a predetermined stroke in a positionally and chronologically correct manner, within one revolution of the main shaft 5. Two control pins 28 or 29 are also provided. The control pins are reciprocatable by a predetermined stroke in a synchronized manner at right angles to the axis of the main shaft 5. They are also connected to an electric, hydraulic or pneumatic operating means including a control unit CU receiving "test" or "skip" commands at terminal C and revolution data, schematically indicated by arrow n(5) of rotation of shaft 5, and they can be brought into and out of control contact, in a positionally and chronologically correct manner, with the respective control path 26 or 27 of one control disc 24 or 25.

Figure 3:
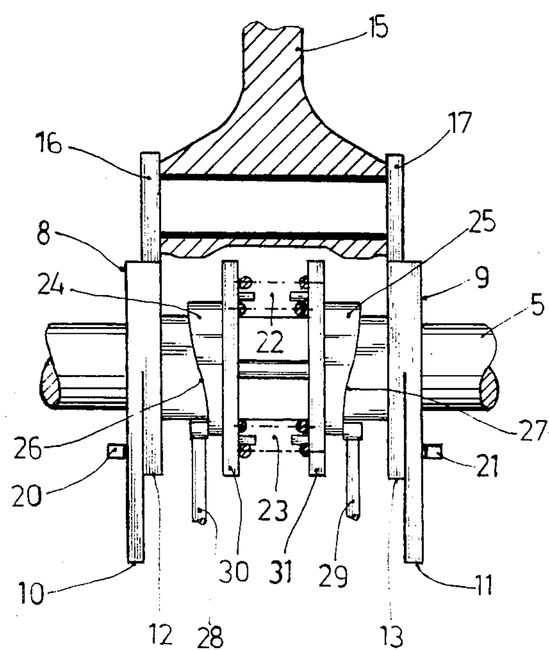
FIG. 3 shows another possible embodiment of the control of the elements in the test apparatus of FIGS. 1 and 2 that execute the pressure generation; again, these elements are shown not in their correct positions but rather shifted by 90° into the plane of the drawing.

Alternatively to the above embodiment, however, the apparatus according to characteristic (c) can also be embodied as shown in FIG. 3. The difference from the embodiment of FIG. 2 is substantially that here the two control discs 24 and 25 are disposed not outside the respective control cams 8 or 9 but rather inside, between the cams 8 and 9. This arrangement of the control discs also necessitates the provision of pressure plates 30 and 31, between which the springs 22 and 23 extend. Furthermore, the piston rod 15 must be widened in the area of the support of the cam follower rollers 16 and 17, and the axial spacing between the cam follower rollers 16 and 17 must also be increased. The continuous control path 26 or 27 is embodied on the respective radially oriented side wall of an undercut on the control disc 24 or 25.

Figure 4:
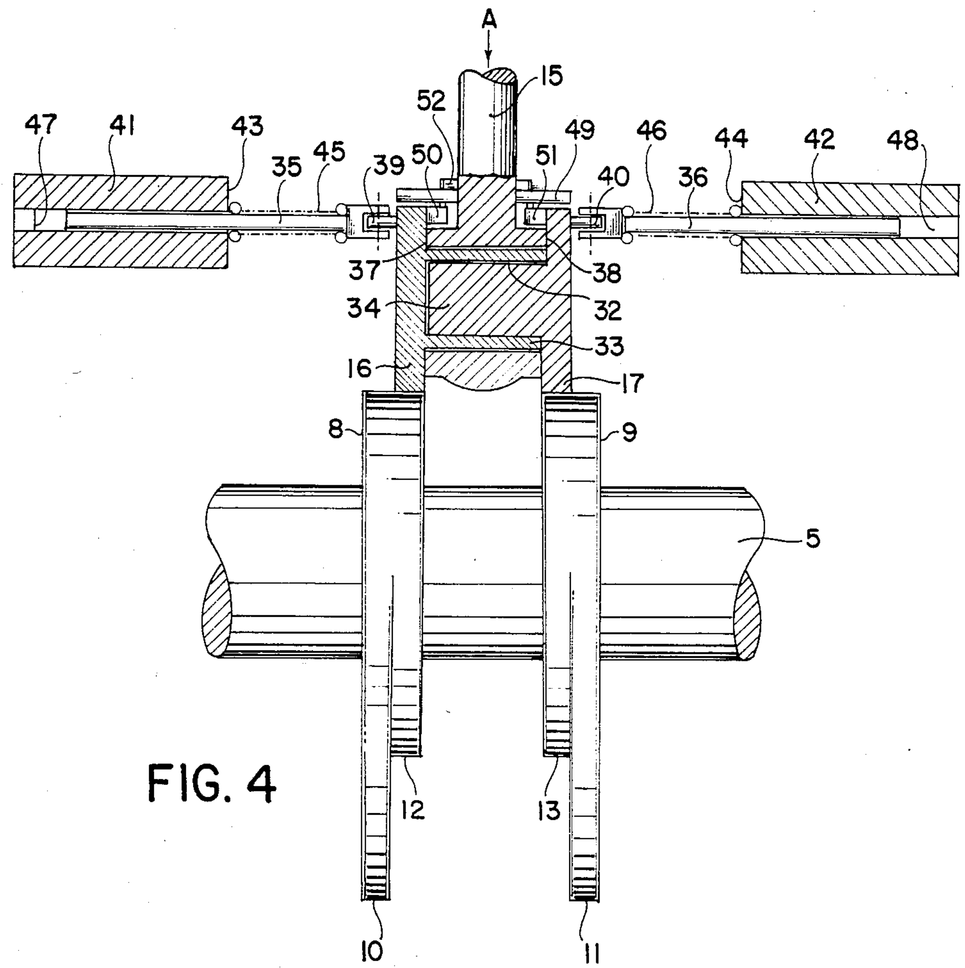
FIG. 4 shows a further possible embodiment of the control of the elements in the test apparatus of FIGS. 1 and 2 that execute the pressure generation, once again not in their correct positions but instead shifted by 90° into the plane of the drawing.
Figure 5:
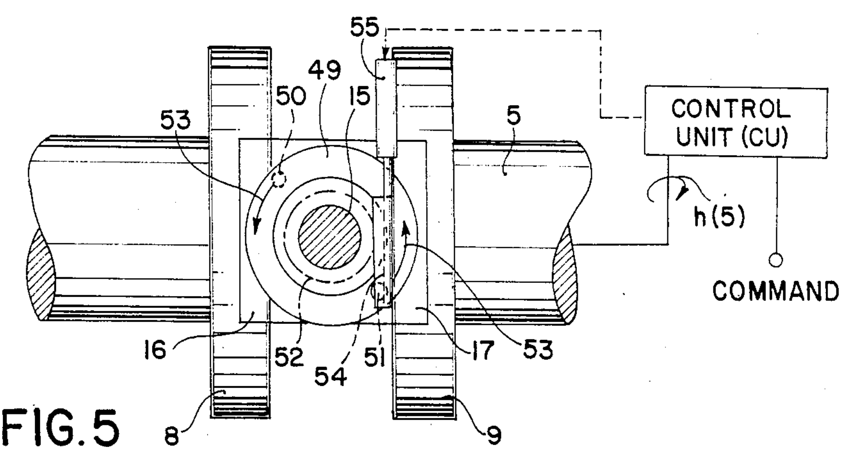
FIG. 5 is another view of the elements of FIG. 4, seen from the direction of the arrow A.

Still another embodiment of the apparatus according to characteristic (c) is shown in FIGS. 4 and 5. According to the principle applied here, it is not the control cams 8 and 9, but rather the cam follower rollers 16 and 17 which are displaced. To this end, the two cam follower rollers 16 and 17 are supported in a transverse bore 32 of the piston rod 15 such that they are axially displaceable with respect to one another, and one cam follower roller 16 has a sleeve 33, which slides in the transverse bore 32 and into which the other cam follower roller 17 enters, engaging it with an axial bolt 34. In this case, both cam follower rollers 16 and 17 are pressed from the outside against lateral stop faces 37 and 38, respectively, of the piston rod 15 by roller tappets 35, 36 which are acted upon by compression springs. In this position, the cam follower rollers 16, 17 travel on the circular portions 12, 13 of the control cams 8, 9. On their ends opposing the rollers 39 and 40, respectively, the roller tappets 35, 36 are each guided in an abutment 41 and 42 secured to the frame and having a contact face 43 and 44 for a respective compression spring 45 and 46 supported at the other end on the head of the roller tappet 35 and 36. Each abutment 41 and 42 also has a respective stop 47 and 48, by means of which the deflection of a given roller tappet 35 or 36 is limited. In this position of the roller tappets 35 and 36, the cam follower rollers 16 and 17 are located in the operative region of the part circular, part land portions 10, 11 of the two control cams 8 and 9. Furthermore, an electrically, hydraulically or pneumatically actuatable reciprocating device having appropriate control means may be provided, by which the cam follower rollers 16 and 17 can be spread apart at the correct time and to the correct position. The reciprocating device may comprise a pressure plate 49 (FIG. 5) rotatably retained on the piston rod 15, and having two diametrically opposed control pins or control rollers 50, 51 on one end, on a sector of a circle, and a pinion 52 on its other end. The control pin or control roller 50 is in sliding contact with the inside of the cam follower roller 16, while the other control pin or control roller 51 is in sliding contact with the inside of the cam follower roller 17. The sector on which the two control pins or control rollers 50, 51 are disposed has a diameter such that when the pressure plate 49 rotates in the direction of the arrow 53 out of the position shown in FIGS. 4 and 5, the two cam follower rollers 16 and 17 are displaceable by the length of that stroke, into a position in which the two cam follower rollers 16 and 17 are in control contact with the part circular, part land portions 10, 11 of the two control cams 8 and 9. For actuating the pressure plate 49, a rack 54 is in turn provided, which is connected to a reciprocating cylinder 55; these elements are also to be considered part of the reciprocating device controlled by a control unit CU. The rack 54 can be moved by a plunger magnet or a cylinder-piston arrangement, for example, or any other suitable operating element well known in engineering design.

The motor 6 is preferably embodied by an appropriately designed electric motor. It is secured on a bottom plate of the frame 1 and drives the fly wheel 7 via belts 56. The belts 56 advantageously engage radial grooves of the fly wheel 7 and thus wrap themselves about the fly wheel 7 over a large portion of its circumference. To assure stable support of the piston rod 15, at least one bearing block 57 is provided, disposed on the frame 1 and having a split slide bearing 58; guide rails 59 disposed in a stationary manner on the frame 1 are also provided, in which support rollers 60 are guided. The support rollers 60 are supported coaxially with and on the same shaft as the cam follower rollers 16 and 17. It is suitable to provide, in addition to the first bearing block 57, in which the piston rod 15 is guided in the vicinity of a cylindrical guide section, a second bearing block 61, which engages the posterior end of the pressure piston 14 and preferably serves as well to fix the position of the hollow body 2, being embodied in accordance with this additional function. The main shaft 5 is composed of two parts, in order to facilitate manufacture and assembly, one part supporting the fly wheel 7 and the other part supporting the two control cams 8 and 9. The two parts of the main shaft 5 are screwed together in the vicinity of two flanges 62, 63.

In the vicinity of their part circular, part land portions 10, 11, the two control cams 8 and 9 are designed for a stroke such as is required so as to enable compressing the medium contained in the hollow body, which by way of example has a compressibility of 1% per 1000 bar pressure loading, to the required high pressure on the order of magnitude of 10,000 bar.

One pressure generating operation will now be described in greater detail. It is assumed that the hollow body 2 is properly fastened in the test apparatus and is filled with the medium required for pressure generation; it is further assumed that all the elements of the apparatus for generating extreme pressure are operationally ready and that the electric motor 6 has already brought the fly wheel 7 to the specified operating speed.

For one pressure generating operation, or event, the cam follower rollers 16 and 17 are then displaced, within a fraction of a second, by the means described above, moving away from the completely circular portions 12, 13 of the control cams 8, 9 and into the operative area of the part circular, part land portions 10 and 11 thereof. This operation takes its course during a one-half revolution of the main shaft 5 and in terms of control is synchronized for the portions of the cams 8 and 9 included between the points 64 and 65 shown in FIG. 1; this is the region in which the contour of the respective cam portion 10 or 11 is identical to that of the circular portions 12 or 13, so a transverse displacement of the cam follower rollers 16, 17 or of the control cams 8, 9 is easily possible. As soon as the cam follower rollers 16 and 17 then come into contact with the region of the part circular, part land portions 10 or 11 of the cams that generate the stroke, the pressure piston 14 is displaced into the interior of the hollow body 2, causing the medium contained therein to be compressed, to an extent which depends on the length of the stroke of the control cams 8, 9 and on the compressibility of the pressure medium. The pressure established thereby is picked up by a detector, not shown, and transmitted to an evaluating device. As soon as the cam follower rollers 16, 17 have passed the highest point on the part circular, part land cam portions 10, 11, the piston rod 15 and hence the pressure piston 14 are pressed back into their initial position, and the pressure is thus released. As the main shaft 5 continues to revolve, as soon as the cam follower rollers 16 and 17 again reach the region of the control cams 8 and 9 shown between the points 64 and 65, the control rollers 16 and 17 are again displaced out of the operative region of the part circular, part land portions 10 and 11, under the control of the unit CU; this event also occurs within a fraction of a second, and in terms of control is synchronized for the angle of rotation range shown between points 64 and 65, as given by input n(5) of the control unit CU.

One operation or event of pressure generation such as that described above elapses within a time period of a total of 50 msec, by way of example; the rotational speed of the fly wheel 7 decreases in accordance with the energy consumed. The motor 6 is, however, designed such that the fly wheel 7 is brought back to the specified operating speed within only a few seconds, so that a new pressure generation operation is again possible. The apparatus for generating extreme pressure according to the invention may for example be designed such that four pressure generation operations having the above-described course can be performed within one minute. In the event that a component unit disposed in the hollow body 2 is to be tested for its stability, then after a sufficient number of pressure generation events it can be ascertained, using suitable methods, whether any changes have taken place in the component being tested or not.

A suitable pressure medium is hydraulic pressure fluid, e.g., of high performance vehicular brake fluid type, or of the aircraft hydraulic fluid type.

We claim:

1. Test apparatus for testing a hollow body (2) having a volume of between about 1 and 10 $dm^3$ with a fluid medium which is compressible within the hollow body with a compressibility of down to about 1% per 1000 bar pressure loading, having a sturdy frame (1);

a test object holder secured to the frame to receive the hollow body (2) and retain said body in fixed position during application of pressure thereto;

and comprising, in accordance with the invention, means for generating extreme pressure, on the order of 10,000 bar within the hollow body and within a fraction of a second including the combination of (a) a drive unit having a fly wheel (7) mounted on the main shaft (5);

a motor (6) driving the fly wheel;

two control cams (8, 9) of mirror symmetrical shape secured to the main shaft (5), each control cam having a complete circular portion (12, 13) and a part circular, part land portion (10, 11) adjacent the complete circular portion;

(b) a pressure generating unit having means (4) for introducing a pressure fluid into said body;

a pressure piston (14) shaped to penetrate the hollow body and to be received therein with essentially no leakage of pressure fluid;

a piston rod (15) movably secured on the frame (1) having one end thereof coupled to the pressure piston;

a pair of cam follower rollers (16, 17) secured to the other end of the piston rod, a respective one of said cam follower rollers being biased for engagement with a respective one of the control cams; and (c) an operating unit for selectively controlling and effecting engagement of the respective cam follower rollers with the respective land portions of the control cams, or the entire circular portion of the control cams, said operating unit being coupled for operation in synchronism with rotation of the main shaft (5) and for selectively controlling operation of the pressure piston during a time which is a fraction of a second.

2. Test apparatus according to claim 1, wherein the operating unit (c) comprises biased springs (22. 23) and wherein (d) the two control cams (8, 9) are secured against twisting but are supported on the main shaft (5) such that they are axially displaceable between two stops (20, 21) fixed to the frame and are spread apart by the springs (22, 23);

(e) a control disc (24, 25) is disposed on the outside of each control cam (8, 9), the end face of the control disc encompassing a continuous control path (26, 27), which is embodied such that the respective control cam (8, 9) is displaceable with a predetermined stroke in a chronologically and positionally correct manner within one revolution of the main shaft (5); and (f) a respective control pin (28, 29) which can be made to reciprocate by a predetermined stroke at right angles to the axis of the main shaft (5) and is connected to an electric, hydraulic or pneumatic operating device with appropriate control means is capable of being brought selectively into and out of control contact, in a chronologically and positionally correct manner, with the respective control path (26, 27) of the control disc (24, 25).

3. Test apparatus according to claim 1, wherein the operating unit (c) comprises biased springs (22, 23) and wherein (g) the two control cams (8, 9) are secured against twisting but are supported on the main shaft (5) such that they are axially displaceable between two stops (20, 21) fixed to the frame and are spread apart by the springs (22, 23);

(h) one control disc (24, 25) having a radially oriented wall face is disposed on the inside of each control cam (8, 9) and has an undercut, the radially oriented wall face of which forms a control path (26, 27), which has a shape such that the respective control cam (8, 9) is displaceable with a predetermined stroke in a chronologically and positionally correct manner within one revolution of the main shaft (5); and (i) a respective control pin (28, 29) which can be made to reciprocate by a predetermined stroke at right angles to the axis of the main shaft (5) and is connected to an electric, hydraulic or pneumatic operating device with appropriate control means is capable of being brought selectively into and out of control contact, in a chronologically and positionally correct manner, with the respective control path of one control disc (24, 25).

4. Test apparatus according to claim 1, wherein in the operating unit (c), (j) the two cam follower rollers (16, 17) are supported such that they are axially displaceable with respect to one another in a transverse bore (32) of the piston rod (15), one cam follower roller (16) having a sleeve (33), which is entered by the other cam follower roller (17) which engages it with an axial bolt (34);

(k) the two cam follower rollers (16, 17) are pressed from the outside by spring-loaded roller tappets (35, 36) against stop faces (37, 38) of the piston rod (15), in which position the cam follower rollers (16, 17) travel on the completely circular portions (12, 13) of the two control cams (8, 9);

(l) the roller tappets (35, 36) are guided, on their ends opposing the rollers (39, 40), in an abutment (41, 42) fixed to the frame, which abutment includes a stop face (43, 44) for a compression spring (45, 46) supported on its other end on the head of one roller tappet (35, 36) and further includes a stop (47, 48), by which the deflection of the respective roller tappet (35, 36) is limited, in which position the cam follower rollers (16, 17) are then located in the operative region of the part circular, part land portions (10, 11) of the two control cams (8, 9); and a reciprocating device comprising at least one of:

(m) an electrically, hydraulically, pneumatically actuatued reciprocating device (49, 50, 51, 52, 54, 55) and appropriate control means is provided, by means of which the cam follower rollers (16, 17) can be spread apart in a chronologically and positionally correct manner.

5. Test apparatus according to claim 1, wherein the control cams (8, 9), in the vicinity of their part circular, part land portions (10, 11), are dimensioned to provide a stroke of the piston which is necessary in order to be able to compress the medium contained in the hollow body (2) to the required high pressure up to the order of magnitude of approximately 10,000 bar.

6. Test apparatus according to claim 1, wherein the motor (6) is an electric motor.

7. Test apparatus according to claim 1 wherein the motor (6) is secured on a bottom plate of the frame (1) and drives the fly wheel (7) via belts (56).

8. Test apparatus according to claim 1, wherein in order to support the piston rod (15) in a stable manner, at least one bearing block (57) is provided disposed on the frame (1) and having a split slide bearing (58) as well as guide rails (59) disposed in a stationary manner on the frame (1), in which guide rails support rollers (60) are guided coaxially with the cam follower rollers and are mounted on the same axis as the cam follower rollers (16, 17).

9. Test apparatus according to claim 8, wherein the piston rod (15), in the vicinity of a cylindrical guide section, is guided by a first bearing block (57) and a second bearing block (61) is provided, said second bearing block encompassing an end of the pressure piston (14).

10. Test apparatus according to claim 9, wherein the second bearing block (61) also serves to positionally fix the hollow body (2) and is embodied in accordance with this additional purpose.

* * * * *